United States Patent [19]

Drake

[11] 4,261,927
[45] Apr. 14, 1981

[54] HYDROGENATION OF OLEFINICALLY UNSATURATED COMPOUNDS

[75] Inventor: Charles A. Drake, Nowata, Okla.

[73] Assignee: Phillips Petroleum Company, Bartlesville, Okla.

[21] Appl. No.: 705,485

[22] Filed: Jul. 15, 1976

[51] Int. Cl.³ .......................... C07C 83/00; C07C 5/02
[52] U.S. Cl. ..................................... 564/491; 585/277
[58] Field of Search ............... 260/409, 683.9, 583 K; 585/277

[56] References Cited

U.S. PATENT DOCUMENTS

| 2,166,971 | 7/1939 | Schmidt et al. | 260/583 K |
|---|---|---|---|
| 2,888,397 | 5/1959 | Burton et al. | 208/138 |
| 2,968,632 | 1/1961 | Kolkins et al. | 252/455 |
| 3,253,040 | 5/1966 | Potter et al. | 260/583 K |
| 3,629,146 | 12/1971 | Adams | 252/435 |
| 3,880,929 | 4/1975 | Drake | 260/583 K |

Primary Examiner—John F. Niebling

[57] ABSTRACT

Olefinically unsaturated compounds are hydrogenated in the presence of a palladium or ruthenium catalyst and a promoter selected from the group consisting of chromium nitrate, barium nitrate and lanthanum nitrate.

25 Claims, No Drawings

HYDROGENATION OF OLEFINICALLY UNSATURATED COMPOUNDS

This invention relates to a process for the hydrogenation of olefinically unsaturated compounds.

In general, various processes for the catalytic hydrogenation of olefinically unsaturated compounds to compounds free of olefinic unsaturation are known to the art. Various materials have been employed as catalysts for the hydrogenation of various feedstocks in these processes. However, the reaction rate and conversion are frequently not as high as would be desirable. Accordingly, there is a continuing search for catalyst materials which will improve the reaction rate and/or conversion level of these processes.

Thus, it is an object of the present invention to provide a new and improved process for the hydrogenation of olefinically unsaturated compounds. Another object of the invention is to increase the conversion level in a process for the hydrogenation of olefinically unsaturated compounds. A further object of the invention is to increase the reaction rate in the conversion of olefinically unsaturated compounds to compounds free of olefinic unsaturation. Yet another object of the invention is to provide for more efficient utilization of palladium and/or ruthenium hydrogenation catalyst in the hydrogenation of compounds containing olefinic unsaturation. Other objects, aspects and advantages of the invention will be apparent from a study of the specification and the appended claims to the invention.

In accordance with the present invention it has been discovered that these objectives can be achieved by conducting the hydrogenation reaction in the presence of a palladium or ruthenium catalyst and at least one promoter selected from the group consisting of chromium nitrate, barium nitrate and lanthanum nitrate.

The olefinically unsaturated compounds for which the present invention is applicable can be represented by the formula $RX_y$ wherein R is a hydrocarbyl radical having from 2 to 50 carbon atoms, at least one olefinic double bond and a valence of y, each X is individually selected from the group consisting of —H, —OR', —C≡N, —CH=NH,

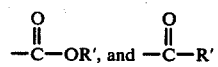

wherein R' is hydrogen or a monovalent hydrocarbyl radical having 1 to 20 carbon atoms, and y is an integer in the range of 1 to 6. R can be aliphatic, cycloaliphatic, aryl substituted aliphatic, aryl substituted cycloaliphatic, aliphatic substituted cycloaliphatic, cycloaliphatic substituted aliphatic, aliphatic substituted aryl, cycloaliphatic substituted aryl, and the like. The R radical can contain a single olefinic double bond or a plurality of olefinic double bonds, and in such instances the olefinic double bonds may be either conjugated or nonconjugated.

The R' radical can be aliphatic, cycloaliphatic, aryl, aryl substituted aliphatic, aryl substituted cycloaliphatic, aliphatic substituted cycloaliphatic, cycloaliphatic substituted aliphatic, aliphatic substituted aryl, cycloaliphatic substituted aryl, and the like. The R' radical can be saturated or unsaturated, and such unsaturation can be in the form of one or more olefinic double bonds and/or aromatic unsaturation. However, it is not intended that aromatic unsaturation be considered as olefinic unsaturation as the aromatic unsaturation is believed to generally be resistant to hydrogenation under the conditions employed in the present process. The X radicals can be hydrogen reducible functional groups such as the nitrile group and the carbonyl group which may be relatively unaffected by the olefinic hydrogenation process or which may be substantially hydrogenated, depending on the hydrogenation conditions selected. The olefinically unsaturated feed should be at least substantially free of halogens and sulfur since these elements generally are effective poisons for the palladium and ruthenium hydrogenation catalysts.

Examples of suitable olefinically unsaturated compounds which can be employed as feed in the present hydrogenation process include ethylene, 1-hexene, 2-decene, 1-tetradecene, 1-eicosene, 1-triacontene, 2-methyl-2-pentene, 1,3-butadiene, 2,3-dimethyl-1,3-butadiene, 3,7-dimethyl-1,3,7-octatriene, 2-phenyl-1,3-butadiene, 1,2-diphenylethylene, 2-buten-1-ol, 9-octadecen-1-ol, 2-methyl-2-butenal, 2-methyl-2-hepten-6-one, 4-methoxy-3-buten-2-one, cinnamonitrile, 5-methyl-4-nononedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, 2,6-dimethyl-4-methyleneheptanedinitrile and the like, and mixtures of any two or more thereof.

The branched-chain olefinically unsaturated nitriles which are considered to be advantageously and efficiently hydrogenated in accordance with the process of this invention have the formula

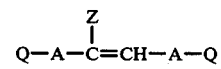

wherein each A is a divalent hydrocarbyl radical, Z is an alkyl radical, and each Q is individually selected from the group consisting of —H and —C≡N with at least one Q being —C≡N. While nitriles having any number of carbon atoms can be employed, in general each A will have from 1 to 15 carbon atoms, preferably from 1 to 6 carbon atoms, and more preferably from 1 to 3 carbon atoms, and Z will have from 1 to 15 carbon atoms, preferably from 1 to 6 carbon atoms, and more preferably from 1 to 3 carbon atoms. Each A can be a saturated acyclic hydrocarbyl radical, a saturated cyclic hydrocarbyl radical, an olefinically unsaturated acyclic hydrocarbyl radical, an olefinically unsaturated cyclic hydrocarbyl radical, or any combination thereof. The cyclic radical can have any desired number of rings, but the cyclic radical will generally be monocyclic. Examples of useful mononitrile compounds include 3-methyl-3-pentenenitrile, 4-methyl-3-pentenenitrile, 2,4,5,5-tetramethyl-3-hexenenitrile, 3,6-diethyl-7-methyl-5,7-octadienenitrile, 4-cyclohexyl-2,2,4-trimethyl-3-pentenenitrile, 6-(3-cyclopentenyl)-4-n-propyl-3-heptenenitrile, 18-methyl-17-eicosenenitrile, and mixtures of any two or more thereof.

The present process is particularly advantageous for the single stage hydrogenation of olefinically unsaturated dinitriles of the formula

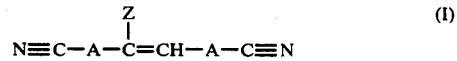

(I)

wherein A and Z are as defined hereinabove. In a presently preferred embodiment each A is individually selected from the group consisting of an alkylene radical and an alkylidene radical. In general, the unsaturated dinitrile reactant of formula (I) will contain from 7 to 30 carbon atoms, preferably from 8 to 16 carbon atoms, and more preferably from 9 to 12 carbon atoms. The branched-chain unsaturated aliphatic dinitriles of formula (I) have been found to be particularly difficult to hydrogenate with many of the conventional hydrogenation catalysts, but can be readily hydrogenated in accordance with the process of the present invention.

Representative unsaturated reactant species of formula (I) include such compounds as 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures of any two or more thereof.

If desired, other nitrile reactants can be present and effectively hydrogenated during the hydrogenation of the unsaturated dinitriles of formula (I). Thus, in addition to the unsaturated dinitrile reactants of formula (I), the dinitrile feedstock can contain one or more olefinically unsaturated dinitrile reactants of the formula

(II)

wherein each J is independently selected from the group consisting of an alkylene radical and an alkylidene radical. In general, each J will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenedpentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures of any two or more thereof.

Nitriles having a structure other than that of formulas (I) and (II) can be present during the hydrogenation of these dinitriles, if desired. Similarly, other compounds which may be found in the feed source of the dinitriles of formulas (I) and (II) can be present so long as such additional compounds do not significantly adversely affect the hydrogenation of the dinitriles of formulas (I) and (II). In a presently preferred process for the hydrogenation of dinitriles of formula (I), the dinitriles of formula (I) generally constitute at least 0.1 weight percent, preferably at least 5 weight percent, and more preferably at least 10 weight percent of the total nitriles in the feedstock.

A presently preferred branched-chain unsaturated aliphatic dinitrile feedstock for employment in the practice of this invention is the dinitrile reaction product mixture of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

The hydrogenation catalysts which can be utilized in the instant invention are those based on palladium or ruthenium or mixtures thereof. For example, the catalyst can be elemental ruthenium, elemental palladium, compounds of ruthenium or palladium which are reducible by hydrogen under the hydrogenation conditions to finely divided elemental ruthenium or palladium, or mixtures of any two or more thereof. Suitable hydrogen reducible compounds include the oxides, halides, nitrates, oxalates, acetates, carbamates, propionates, tartrates, hydroxides, and the like and mixtures of any two or more thereof. Specific examples of suitable catalysts include elemental ruthenium, ruthenium oxide, ruthenium chloride, ruthenium nitrate, ruthenium acetate, ruthenium carbonate, ruthenium hydroxide, elemental palladium, palladium oxide, palladium chloride, palladium nitrate, palladium oxalate, palladium acetate, palladium carbamate and palladium hydroxide, and the like, and mixtures of any two or more thereof.

In the practice of this invention, it is often desirable to employ catalytic amounts of elemental ruthenium, elemental palladium, hydrogen reducible compounds of palladium or ruthenium, or mixtures thereof on a solid catalyst carrier which does not deleteriously affect the catalytic hydrogenation process of this invention. Such supports include, for example, carbon, kieselguhr, silica, alumina, silica-alumina, calcium carbonate, barium carbonate, asbestos, pumice, clays, and the like, and mixtures of any two or more thereof. The ruthenium or palladium can be added to the catalyst support by any of the methods well known in the art. For example, the supported catalyst can be prepared by dry mixing the components or by impregnating the support with a solution or dispersion of ruthenium or palladium in elemental form or in the form of reducible compounds thereof. The supported catalysts can be pretreated with hydrogen to reduce the palladium or ruthenium compounds, or such reduction can be achieved in the hydrogenation reactor. When a support is employed, the amount of ruthenium and/or palladium on the support material will generally be in the range of about 0.05 to about 50, preferably in the range of about 0.5 to 20, and more preferably in the range of about 0.1 to about 10 weight percent, based on the weight of the total catalyst composition. Examples of suitable catalysts include ruthenium or palladium on alumina, each having a catalyst component metal content of about 5% by weight based on the total weight of the catalyst component and support material. Other suitable catalysts include palladium on charcoal (10% palladium), ruthenium dioxide, and ruthenium on charcoal (5%). The specifically named catalysts are commercially available catalytic materials.

The amount of catalyst employed in the hydrogenation process of the instant invention can be any amount which is catalytically effective for the hydrogen reaction. The amount of catalyst can be expressed in terms of the weight ratio of the ruthenium and/or palladium catalyst, expressed as elemental metal, to the olefinically unsaturated compound being hydrogenated. This ratio can be any suitable value, but generally will be in the range of about 0.001/1 to about 0.5/1, preferably in the range of about 0.0002/1 to about 0.2/1, and more preferably in the range of about 0.0005/1 to about 0.1/1.

According to the instant invention, a hydrogenation promoting effective amount of at least one metal nitrate promoter selected from the group consisting of the nitrates of chromium, barium, and lanthanum is employed to improve the efficiency of the catalytic hydrogenation using a catalyst of palladium and/or ruthenium described above. The metal nitrate promoter selected from the group consisting of chromium, barium and lanthanum nitrates and mixtures of any two or more thereof, can be added to the hydrogenation reaction mixture in any suitable manner according to the instant invention. It may be added with the diluent, if one is employed, or simply added to the olefinically unsaturated compound feedstock. Solubility of the metal nitrate promoter in the diluent, if employed, or in the feedstock is not required in the utilization of the metal nitrate promoters.

The amount of metal nitrate promoter utilized in the instant invention can be any amount which is effective in promoting the catalytic hydrogenation of the olefinically unsaturated compounds. This amount can be conveniently expressed in terms of a weight ratio of the catalytic metal, i.e. palladium and/or ruthenium expressed as elemental metal, to the weight of the metal nitrate promoter utilized. While any suitable value for this ratio can be employed, this weight ratio will generally be in the range of about 0.005/1 to about 1/1, preferably in the range of about 0.01/1 to about 0.8/1, and more preferably in the range of about 0.015/1 to about 0.4/1 for chromium nitrate. For barium nitrate this ratio will generally be in the range of about 0.5/1 to about 1/1, preferably in the range of about 0.05/1 to about 0.8/1, and more preferably in the range of about 0.1/1 to about 0.4/1. For lanthanum nitrate, this ratio will generally be in the range of about 0.1/1 to about 1/1, preferably in the range of about 0.1/1 to about 0.8/1, and more preferably in the range of about 0.15/1 to about 0.4/1.

The hydrogenation reaction can be conducted at any suitable reaction conditions. In general the hydrogenation reaction will be conducted under liquid phase conditions. Any catalytic hydrogenation temperature can be employed which provides the desired degree of catalytic efficiency in the hydrogenation of the olefinically unsaturated compound containing feedstock. The hydrogenation temperatures will generally be within the range of about 20° to about 300° C., preferably within the range of about 20° to about 200° C., and more preferably within the range of about 20° to about 150° C. However, when the reaction temperature employed is in the low end of the temperature range, it is considered desirable, if not necessary to employ higher hydrogen pressures and/or longer reaction times in order to readily achieve the desired degree of hydrogenation.

The catalytic hydrogenation of the olefinically unsaturated compounds can be carried out at any hydrogen pressure at which significant reduction of the olefinic double bond occurs. In general, the hydrogen pressure will be within the range of about 100 to about 35,000 kiloPascals (kPa), preferably in the range of about 200 to about 30,000 kPa, and more preferably in the range of about 275 to about 17,500 kPa.

Any time interval suited for the catalytic hydrogenation of the olefinically unsaturation can be employed in the practice of this invention. However, time intervals economically attractive to the process are generally within the range of about 10 minutes to about 30 hours for a batch hydrogenation process. A reaction time in the range of about 30 minutes to about 12 hours is presently preferred in order to insure at least substantially complete hydrogenation of the olefinic bonds in the feedstock. The catalytic hydrogenation of olefinically unsaturated compounds in accordance with the process of this invention can be carried out as a continuous process at any suitable liquid hourly space velocity (LHSV). However, the liquid hourly space velocity rates will generally be within the range of about 0.1 to about 10, more preferably from about 0.5 to about 2, volumes of olefinically unsaturated reactant plus diluent per volume of catalyst (including the volume of any catalyst support if any is present).

The effects of the temperature, pressure and reaction time employed in the hydrogenation process are generally interrelated, and it is within the routine skill to determine suitable ranges for any two of these variables for a given value of the third variable.

It is desirable that the hydrogenation reaction be carried out in the presence of a suitable diluent. While any suitable diluent can be employed, it is preferable that the diluent be selected from the class consisting of unsubstituted alkanols containing from 1 to 12 carbon atoms per molecule, unsubstituted acyclic and unsubstituted cyclic ethers having 4 to 12 carbon atoms per molecule, saturated hydrocarbons having 4 to 12 carbon atoms per molecule, and mixtures of any two or more thereof. The term "unsubstituted" indicates that there are no substituents other than hydrocarbyl radicals. Examples of alkanol diluents include methanol, ethanol, propanol, 2-methyl-2-propanol, 2-methyl-2-butanol, 2-methyl-2-pentanol, 2-ethyl-2-hexanol, 3-ethyl-3-hexanol, 2,4-dimethyl-2-pentanol, 2,3-dimethyl-3-pentanol, 3,6-diethyl-3-octanol, and the like, and mixtures of any two or more thereof. Examples of alkanes and cycloalkanes include butane, pentane, hexane, decane, dodecane, cyclobutane, cyclopentane, cyclohexane, cyclodecane, cyclododecane, 2-methylbutane, methylcyclopentane, 2,2,4-trimethylpentane, and mixtures of any two or more thereof. Examples of ethers include diethyl ether, 1,3-dioxane, 1,4-dioxane, tetrahydrofuran, 4,4-dimethyl-1,3-dioxane, and mixtures of any two or more thereof. To facilitate handling of the reaction mixtures, the weight ratio of olefinically unsaturated reactants to diluent charged to the particular reaction zone is generally within the range of about 0.001:100 to about 20:100, and is preferably in the range of about 0.1:100 to about 15:100.

Processing of the effluent from the hydrogenation reaction for the recovery of the desired end product, as well as any resulting reaction byproducts, any unconsumed reactants, hydrogen, and/or diluents can be carried out by any conventional separation means. In general, at the conclusion of the catalytic hydrogenation process, the reaction effluent is cooled and depressurized with the recovery, if desired, of any diluent, product or reactant which is vented from the reaction effluent during the depressurization operation. The diluent and/or reactant can be returned or recycled to the hydrogenation reaction if desired. The reaction products can be separated from the catalyst by conventional filtration means. The filtrate containing the compounds at least substantially completely free of olefinic unsaturation can be conveniently separated from any reaction byproducts or any diluent remaining in the filtrate by any conventional fractional distillation.

The use of the metal nitrate promoters according to the instant invention appears to exert an accelerating effect on the rate of hydrogenation of the olefinic unsaturation. Thus, the use of the metal nitrate promoters should allow hydrogenation of a wide variety of olefinic substrates at more moderate reaction conditions than normally utilized. In other words, a more efficient use of a given amount of expensive palladium and/or ruthenium hydrogenation catalyst is obtained when utilizing the metal nitrate promoters according to the instant invention. Such improvement in the efficient utilization of expensive catalysts is an obviously desirable result in hydrogenation processes.

The following examples are presented in further illustration of the invention and should no be construed in undue limitation thereof. In Examples I, II and III, the olefinic substrate which is undergoing hydrogenation is an unsaturated dinitrile mixture obtained by the reaction of isobutylene and acrylonitrile. This unsaturated dinitrile mixture comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. For convenience, the above mixture will be described as diadduct in these examples. The above described diadduct can be hydrogenated to produce a valuable saturated diamine for use in the preparation of polyamides and other polymers. In such applications, it has been found highly desirable that essentially none of the olefinic unsaturation remains in the final hydrogenation product. It is thus important that the carbon-carbon olefinic double bonds in the diadduct be reduced efficiently in the hydrogenation process employed.

EXAMPLE I

Three runs were conducted employing a two step hydrogenation process for the hydrogenation of diadduct. In the first step, the hydrogenation of the olefinic unsaturation is carried out in the absence of any secondary amine formation suppressant and in the second step, employing a different catalyst and in the presence of ammonia, the hydrogenation of the nitrile groups is conducted. The analysis of the hydrogenation product from the second step is carried out to provide an indication of the extent of hydrogenation of the olefinic unsaturation in the original diadduct. It has been found that the analysis of olefinic unsaturation is more accurate when carried out on the diamine than on the intermediate dinitrile. Each of the three runs was carried out in a one liter autoclave on which was charged 30 grams of diadduct, 3 grams of palladium on alumina (5 wt. % palladium) and 350 ml of methanol. The hydrogenation system was flushed with nitrogen, pressured to 1500 psig (10,300 kPa) with hydrogen and heated at 120° C. with stirring for 2 hours. Each reaction mixture was then filtered, placed in an autoclave along with one teaspoon (about 25 grams) of Raney nickel, and about 30 grams of ammonia (Run No. 1 utilized 25 grams of ammonia), pressured to 1500 psig (10,300 kPa) with hydrogen, and heated at 130° C. for 2 hours. The hydrogenation product from the second step was then analyzed by gas-liquid phase chromatography in order to determine the extent of olefinic reduction that had occurred in the first step of the hydrogenation. The results of the three runs are presented below in Table I along with the amounts of promoter employed in Runs 2 and 3.

TABLE I

| Run No. | Promoter, Amount | Extent of Olefinic Hydrogenation[a] |
|---|---|---|
| 1 | None | 60% |
| 2 | Chromium Nitrate, 0.25 g | 95% |
| 3[b] | Chromium Nitrate, 0.25 g | 95% |

[a]Expressed as extent of hydrogenation based on theoretical complete olefinic hydrogenation.
[b]Duplicate of Run 2.

A comparison of runs 2 and 3 with run 1 readily indicates the substantial effectiveness of the chromium nitrate as a promoter for the palladium catalyst for the hydrogenation of olefinic unsaturation.

EXAMPLE II

Two runs were carried out in which the diadduct was hydrogenated in a one step process employing as catalyst ruthenium on alumina (5 wt. % ruthenium) for the hydrogenation of diadduct to saturated diamine. Each run was carried out in a one liter autoclave which was charged with 30 grams of the diadduct, 1 gram of the above ruthenium catalyst and 350 ml of 2-methyl-2-propanol. The reaction system was flushed with nitrogen, charged with 30 grams of ammonia, pressured to 1500 psig (10,300 kPa) with hydrogen and heated at 170° C. for 2.5 hours. The reaction mixture was filtered and fractionally distilled to recover the hydrogenation product which was analyzed for extent of hydrogenation by gas-liquid phase chromatography. The results obtained in these two runs are presented in Table II below.

TABLE II

| Run No. | Promoter, Amount | Extent of Olefinic Hydrogenation[a] |
|---|---|---|
| 4 | None | 30% |
| 5 | Chromium Nitrate, 0.2 g | 95% |

[a]Expressed as extent of hydrogenation based on theoretical complete olefinic hydrogenation.

A comparison of runs 4 and 5 readily demonstrates the substantial effectiveness of chromium nitrate as a promoter for the ruthenium catalyst for the hydrogenation of olefinic unsaturation.

EXAMPLE III

A series of runs was carried out employing a low pressure hydrogenation procedure with a palladium on alumina catalyst (5 wt. % palladium). Product analysis in the first run of the series assured that the hydrogen uptake under the conditions employed was due to the olefinic unsaturation in the diadduct employed as a feed rather than both olefinic and nitrile hydrogenation. In each of the runs, the hydrogenation reactor was charged with 0.5 grams of said palladium hydrogenation catalyst, 5 grams of diadduct and 150 ml of methanol. As indicated in Table III below, a variety of compounds were tested for their promoting effectiveness on the hydrogenation of the olefinic unsaturation in the diadduct and other runs were conducted which employed no additive as a promoting agent. In each of the runs, the hydrogenation was conducted at the same temperature (about 25° C.) under an initial hydrogen pressure of 40 psig (275 kPa), and the effectiveness of the various compounds as promoting agents was observed by measuring the pressure drop for a given 30 minute period in each run. Thus, for example, an effective promoter would show a greater pressure drop for the 30 minute period than no promoter at all, while another compound which was not an effective promoter would show essentially no change in the pressure drop from that of the control. On the other hand, if the pressure drop was actually less than the control, the added compound was actually functioning under such conditions as a catalyst poison or an inhibitor. The results of this series of runs are presented below in Table III.

TABLE III

| Run No. | Promoter, Amount | Wt. Ratio Pd/Promoter | Pressure Drop, psi |
|---|---|---|---|
| 6 | None | — | 13.0 |
| 7 | None | — | 13.9 |
| 8 | Nickel Nitrate, 0.1 g | 0.25 | 9.5 |
| 9 | Ammonium Nitrate, 0.1 g | 0.25 | 13.1 |
| 10 | Chromium Chloride, 0.1 g | 0.25 | 8.0 |
| 11 | Chromium Nitrate, 0.1 g | 0.25 | 20.4 |
| 12 | Chromium Nitrate, 0.1 g | 0.25 | 23.3 |
| 13 | Chromium Nitrate, 0.1 g | 0.25 | 20.2 |
| 14 | Chromium Nitrate, 0.2 g | 0.125 | 21.3 |
| 15 | Barium Nitrate, 0.1 g | 0.25 | 20.0 |
| 16 | Barium Nitrate, 0.4 g | 0.062 | 14.7 |
| 17 | Lanthanum Nitrate, 0.1 g | 0.25 | 21.0 |
| 18 | Lanthanum Nitrate, 0.4 g | 0.062 | 12.0 |

The results of Table III demonstrate the effectiveness of the nitrates of chromium, barium and lanthanum as promoters for the hydrogenation of olefinic unsaturation with a palladium on alumina catalyst. It is also seen that nickel nitrate and ammonium nitrate were either inhibitors or poisons or ineffective as hydrogenation promoters and that chromium chloride was an inhibitor or poison for the hydrogenation of diadduct under the conditions employed.

The result of Run 18 demonstrates that an amount of lanthanum nitrate promoter outside the preferred range actually produced a slight poisoning or inhibiting effect on the hydrogenation. Although the result of Run 16 is still slightly better than the control runs 6 and 7, the deleterious effect of too much promoter is evident in this run also.

EXAMPLE IV

A series of runs was carried out employing a low pressure hydrogenation procedure with various catalysts with and without chromium nitrate present as a promoter. In each run, the hydrogenation reactor was charged with 0.5 gram catalyst, 150 ml methanol, 5 grams 2-methyl-2-butene and promoter, if employed, under a blanket of nitrogen. In runs 19–24, 5 grams of ammonia was bubbled into the liquid. The reactor was then flushed once with hydrogen by pressuring to 20 psig (137 kPa) and then venting. The reactor was then pressured to 40 psig (275 kPa) and agitation was begun. In each run the hydrogenation was conducted at the same temperature (about 25° C.), and the effectiveness of the various systems was observed by measuring the pressure drop for a given period in each run. In runs 25–32, the reactor was repressured to 40 psig (275 kPa each time the pressure fell below about 10 psig (69 kPa). The results of this series of runs are presented below in Table IV.

TABLE IV

| Run No. | Catalyst | $NH_3$, g. | Wt. Ratio Catalyst[d]/Promoter | Promoter | Pressure drop, psi | Time, min. |
|---|---|---|---|---|---|---|
| 19 | nickel[a] | 5 | — | none | 1.6 | 30 |
| 20 | platinum[b] | 5 | — | none | 4.2 | 30 |
| 21 | palladium[c] | 5 | — | none | 7.2 | 30 |
| 22 | nickel[a] | 5 | 0.33 | chromium nitrate | 1.1 | 30 |
| 23 | platinum[b] | 5 | 0.05 | chromium nitrate | 4.0 | 30 |
| 24 | palladium[c] | 5 | 0.05 | chromium nitrate | 8.0 | 30 |
| 25 | palladium[c] | 0 | — | none | 67 | 15 |
| 26 | palladium[c] | 0 | 0.05 | sodium nitrate | 51 | 15 |
| 27 | palladium[c] | 0 | 0.05 | nickel nitrate | 52 | 15 |
| 28 | palladium[c] | 0 | 0.05 | aluminum nitrate | 52 | 15 |
| 29 | palladium[c] | 0 | — | none | 68.4 | 15 |
| 30 | palladium[c] | 0 | 0.05 | chromium nitrate | 86.2 | 15 |
| 31 | palladium[c] | 0 | 0.125 | chromium nitrate | 75.2 | 15 |
| 32 | palladium[c] | 0 | 0.025 | chromium nitrate | 80.5 | 15 |

[a]33 weight percent nickel on a refractory support.
[b]5 weight percent platinum on alumina.
[c]5 weight percent palladium on alumina.
[d]Based on weight of catalytic element.

The results of Table IV indicate that chromium nitrate is not a promoter for nickel or platinum catalysts for the hydrogenation of olefinic unsaturation while chromium nitrate does promote this reaction for a palladium catalyst. A comparison of runs 21 and 25 reveals the importance of employing the palladium catalyst in the absence of a secondary amine formation suppressant such as ammonia. Runs 25 to 28 indicate the criticality in the selection of the nitrate compound to be employed.

Reasonable variations and modifications are possible within the scope of the foregoing disclosure and the appended claims to the invention.

I claim:

1. A process for the catalytic hydrogenation of at least one olefinically unsaturated compound having the formula $$RX_y$$

wherein R is a hydrocarbyl radical having from 2 to 50 carbon atoms, at least one olefinic double bond and a valence of y, each X is individually selected from the group consisting of —H, —C≡N, and —CH=NH, wherein y is an integer in the range of 1 to 6; which comprises contacting said at least one olefinically unsaturated compound with hydrogen, a catalyst and at least one metal nitrate under reaction conditions suitable to convert at least a substantial proportion of said at least one olefinically unsaturated compound to a product compound free of olefinic unsaturation; said catalyst comprising at least one component selected from the group consisting of elemental palladium, elemental ruthenium, compounds of palladium which are reducible by hydrogen to elemental palladium at said reaction conditions and compounds of ruthenium which are reducible by hydrogen to elemental ruthenium at said reaction conditions; said at least one metal nitrate being at least one member selected from the group consisting of chromium nitrate, barium nitrate and lanthanum nitrate, wherein the amount of chromium nitrate employed based on the weight ratio of catalyst, calculated as elemental metal, to chromium nitrate is in the range of about 0.005:1 to about 1:1,
  wherein the amount of barium nitrate employed based on the weight ratio of catalyst, calculated as elemental metal, to barium nitrate is in the range of about 0.05:1 to about 1:1, and
  wherein the amount of lanthanum nitrate employed based on the weight ratio of catalyst, calculated as elemental metal, to lanthanum nitrate is in the range of about 0.1:1 to about 1:1.

2. A process in accordance with claim 1 wherein said metal nitrate is chromium nitrate.

3. A process in accordance with claim 1 wherein said metal nitrate is barium nitrate.

4. A process in accordance with claim 1 wherein said metal nitrate is lanthanum nitrate.

5. A process in accordance with claim 1 wherein R has from 4 to 20 carbon atoms and R' is hydrogen or a hydrocarbyl radical having 1 to 5 carbon atoms.

6. A process in accordance with claim 5 wherein each X is —H.

7. A process in accordance with claim 5 wherein each X is —C≡N.

8. A process in accordance with claim 7 wherein said at least one olefinically unsaturated compound has the formula

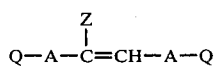

wherein each A is a divalent hydrocarbyl radical, Z is an alkyl radical, and each Q is individually selected from the group consisting of —H and —C≡N with at least one Q being —C≡N; and wherein said contacting is conducted in the at least substantial absence of ammonia.

9. A process in accordance with claim 8 wherein said at least one metal nitrate consists essentially of chromium nitrate.

10. A process in accordance with claim 8 wherein said at least one metal nitrate consists essentially of barium nitrate.

11. A process in accordance with claim 8 wherein said at least one metal nitrate consists essentially of lanthanum nitrate.

12. A process in accordance with claim 5 wherein each X is —CH=NH.

13. A process in accordance with claim 1 wherein said contacting is conducted in the at least substantial absence of a secondary amine formation suppressant.

14. A process in accordance with claim 1 wherein said metal nitrate comprises barium nitrate, and wherein the weight ratio of said catalyst, expressed as elemental metal, to said barium nitrate is in the range of about 0.05/1 to about 0.8/1.

15. A process in accordance with claim 1 wherein said metal nitrate comprises lanthanum nitrate, and wherein the weight ratio of said catalyst, expressed as elemental metal, to said lanthanum nitrate is in the range of about 0.1/1 to about 0.8/1.

16. A process in accordance with claim 1 wherein said metal nitrate comprises chromium nitrate, and wherein the weight ratio of said catalyst, expressed as elemental metal, to said chromium nitrate is in the range of about 0.015/1 to about 0.8/1.

17. A process in accordance with claim 16 wherein said reaction conditions comprise a temperature in the range of about 20° to about 300° C.; a pressure in the range of about 100 to about 35,000 kiloPascals; a time in the range of about 10 minutes to about 30 hours; and a weight ratio of catalyst, expressed as elemental metal, to said at least one olefinically unsaturated compound in the range of about 0.0001/1 to about 0.5/1.

18. A process in accordance with claim 17 wherein said catalyst consists essentially of at least one component selected from the group consisting of ruthenium and said compounds of ruthenium.

19. A process in accordance with claim 17 wherein said catalyst consists essentially of at least one component selected from the group consisting of palladium and said compounds of palladium.

20. A process in accordance with claim 19 wherein said at least one olefinically unsaturated compound comprises 2-methyl-2-butene.

21. A process in accordance with claim 19 wherein said at least one olefinically unsaturated compound comprises 5-methyl-4-nonenedinitrile.

22. A process in accordance with claim 21 wherein said at least one metal nitrate consists essentially of chromium nitrate.

23. A process in accordance with claim 1 wherein said at least one metal nitrate consists essentially of chromium nitrate, and wherein the weight ratio of said catalyst, expressed as elemental metal, to said chromium nitrate is in the range of about 0.015/1 to about 0.4/1.

24. A process in accordance with claim 1 wherein said at least one metal nitrate consists essentially of barium nitrate, and wherein the weight ratio of said catalyst, expressed as elemental metal, to said barium nitrate is in the range of about 0.1/1 to about 0.4/1.

25. A process in accordance with claim 1 wherein said at least one metal nitrate consists essentially of lanthanum nitrate, and wherein the weight ratio of said catalyst, expressed as elemental metal, to said lanthanum nitrate is in the range of about 0.15/1 to about 0.4/1.

* * * * *